United States Patent [19]
Rentsch

[11] Patent Number: 5,387,417
[45] Date of Patent: Feb. 7, 1995

[54] NON-GREASY PETROLATUM EMULSION

[75] Inventor: Stefan F. Rentsch, Midland, Mich.

[73] Assignee: Dow Corning Corporation, Midland, Mich.

[21] Appl. No.: 751,361

[22] Filed: Aug. 22, 1991

[51] Int. Cl.$^6$ ................................. A61K 7/00
[52] U.S. Cl. ..................... 424/401; 514/844; 514/847; 514/937; 514/938; 514/941
[58] Field of Search ............... 424/401, 78; 514/937, 514/938, 941, 844, 847

[56] References Cited

U.S. PATENT DOCUMENTS

| | | | |
|---|---|---|---|
| 2,868,824 | 1/1959 | Haluska | 260/448.2 |
| 3,392,040 | 7/1968 | Kass | 106/287 |
| 3,609,102 | 9/1971 | Schlossman | 252/522 |
| 3,981,990 | 9/1976 | Kelly et al. | 424/78 |
| 4,122,029 | 10/1978 | Gee et al. | 252/309 |
| 4,137,302 | 1/1979 | Humbert et al. | 424/47 |
| 4,152,416 | 5/1979 | Spitzer et al. | 424/46 |
| 4,532,132 | 7/1985 | Keil | 514/937 |
| 4,720,353 | 1/1988 | Bell | 514/937 |
| 4,801,447 | 1/1989 | Green | 424/70 |
| 4,853,474 | 8/1989 | Bahr et al. | 556/445 |
| 5,008,103 | 4/1991 | Raleigh et al. | 424/69 |

FOREIGN PATENT DOCUMENTS 0331833 9/1989 European Pat. Off. ....... A61K 7/00

*Primary Examiner*—Thurman K. Page
*Assistant Examiner*—Amy Hulina
*Attorney, Agent, or Firm*—James L. DeCesare

[57] ABSTRACT

This invention relates to an improved skin care composition for moisturizing and conditioning the skin. In particular, it relates to a cosmetically acceptable, translucent skin conditioning lotion having an emulsified petrolatum base. The emulsions of the present invention are prepared using a crosslinked organopolysiloxane-polyoxyalkylene emulsifier and involve matching the refractive indices for the continuous and discontinuous phases.

4 Claims, No Drawings

NON-GREASY PETROLATUM EMULSION

BACKGROUND OF THE INVENTION

This invention relates to an improved skin care composition for moisturizing and conditioning the skin. In particular, it relates to a cosmetically acceptable, translucent skin moisturizing lotion having an emulsified petrolatum base. The emulsions of the present invention are prepared using a crosslinked organopolysiloxane-polyoxyalkylene emulsifier and involve matching the refractive indices for the continuous and discontinuous phases.

Consumers have long desired a moisturizing and conditioning preparation in the form of a hand and body lotion which, when applied, provides cosmetically acceptable tactile properties. The desirable properties of petrolatum have long been recognized primarily because of its beneficial effects on the skin. Such benefits are neutral, stable, translucent, odorless and substantially non-volatile at atmospheric conditions.

Petrolatum has been used both alone, and as an ingredient in skin care products, for over 60 years. It is believed to be helpful in skin care, because it is occlusive and causes moisture to accumulate in the stratum corneum. It is well known that petrolatum is a moisturizer. Petrolatum is a tenacious substance which stays in place, filling in the irregularities and smoothing the surface of the skin for many hours.

However, it has lone been known that petrolatum is extremely difficult to formulate in a pleasing aesthetic state and therefore, it is not present in many commercially available skin care products. Petrolatum or petroleum jelly impart to the skin an uncomfortable feeling of warmth in addition to a sticky, oily, greasy or waxy feel. Attempts have been made to emulsify petrolatum in a cream or lotion form in order to reduce its greasy and unacceptable tactile properties, when applied to the skin. However, by adding conventional water-soluble detergent emulsifiers to stabilize the petrolatum, the moisturizing properties of the petrolatum are unacceptably reduced.

A satisfactory skin care composition having superior moisturizing and conditioning properties with cosmetically acceptable tactile properties should exhibit satisfactory feel, lubricity and absorption when applied to the skin. In particular, the composition should exhibit good consistency, should apply evenly to the skin, should be absorbed rapidly and should dry quickly. After application, the skin should feel smooth and clean. The composition should assist in relieving the tight feeling of dry skin and should soothe irritated skin.

Until now, prior art and commercially available cosmetic formulations have failed to achieve all the aforementioned desired properties. In U.S. Pat. No. 4,137,302 there is disclosed a composition including cetyl alcohol, isopropyl palmitate and petrolatum. Various cationic emulsifiers are also disclosed. Cosmetic compositions containing petrolatum in combination with the usual cosmetic ingredients are disclosed in U.S. Pat. Nos. 3,392,040, 3,609,102 and 3,981,990. In general, such compositions provide a film which is palpably oily and greasy to the touch upon application.

There is therefore a continuing need for the development of new and improved skin moisturizing compositions which impart beneficial effects to the skin.

SUMMARY OF THE INVENTION

It is an object of the present invention to provide a skin care composition free of the defects and deficiencies of the prior art which provides enhanced moisturizing and conditioning properties while exhibiting cosmetically acceptable tactile properties.

It is another object of this invention to provide stable emulsions of polar liquids in non-polar liquids using a crosslinked organopolysiloxane-polyoxyalkylene emulsifier.

The compositions of the present invention may be applied to the skin, i.e., the arms, the legs, the entire body, where moisturizing or treatment is desired, by smoothing it over the skin. The compositions provide a flexible, non-flaking film on the skin which is free of any sticky, oily, greasy or waxy feel. Moreover, the film provides for high resistance to removal by water or abrasion.

These and other objects are realized by the compositions of this invention wherein a polar liquid is dispersed in a non-polar base using a crosslinked organopolysiloxane-polyoxyalkylene emulsifier. The non-polar base comprises petrolatum.

DETAILED DESCRIPTION OF THE INVENTION

The present invention relates to an emulsion composition comprising:
(I) a discontinuous phase comprising
  (a) a polar liquid, optionally containing dissolved inorganic salt(s);
(II) a continuous phase comprising
  (b) petrolatum;
  (c) a cyclic polydimethylsiloxane fluid; and
  (d) at least two organopolysiloxane-polyoxyalkylene molecules crosslinked by a crosslinking radical.

POLAR LIQUID (a)

Polar liquid (a) of the compositions of this invention is the dispersed phase therein and may comprise one or more efficacious components such as a preservative, an odorant, a deodorant, an antiseptic, a sunscreen agent, a suitable pharmaceutical, or the like.

The polar liquid (a) may be any suitable liquid composition which is insoluble at room temperature in the petrolatum (b), hereinafter described. By polar it is meant a substance which has a permanent dipole moment. Of course, to maintain the identity of the compositions of this invention the polar liquid should not undergo chemical reaction with remaining components of the composition. The polar liquid may be a pure liquid or a liquid solution or a mixture of immiscible liquids, the components of which are polar and insoluble in the petrolatum. Solid polar materials may be used as component (a) if they are changed to a liquid form such as by heating to melt the solid or by dissolving the solid in a solvent.

Examples of suitable materials which are polar include inorganic materials such as water, salts, weak acids and weak bases, and aqueous solutions thereof, and organic materials bearing polar groups such as organic compounds bearing nitrogen-containing groups such as in amides, amines, amine salts, nitriles, imides, imines, lactams, and nitro compounds; oxygen-containing groups such as in alcohols, ethers, and in carbonyl groups such as in ketones, aldehydes, carboxylic acids and their salts, esters and lactones; phosphorus-containing groups such as in phosphates and phosphonium salts; sulfur-containing groups such as in sulfones, mercaptans, sulfoxides and sulfides; and halogens such as in hydrocarbon chlorides, bromides, and iodides. The presence of said polar groups in the organic material provides a permanent dipole moment and thus provides the polar character in the organic material.

Polar liquids (a) of particular interest for the compositions of this invention are therefore selected from the group consisting of water, water solutions of polar solutes, polar liquids soluble in water, ethanol, ethanol solutions of polar solutes and polar liquids soluble in ethanol. Suitable water solutions comprise, as the polar solute, inorganic solutes hereinbefore exemplified and organic solutes such as alcohols which include glycerin, methanol, ethanol, phenol, ethylene glycol, propylene glycol, glycerin, and their partial ethers and partial esters; nitrogen compounds such as amides such as formamide, acetamide, N-methylacetamide, N,N-dimethyl formamide and urea, nitriles such as acetonitrile and amines and their salts, acids such as formic acid, acetic acid, benzoic acid, stearic acid, and ethylenediaminetetracetic acid and ethers such as furan, tetrahydrofuran, dioxane, ethylene glycol dimethyl ether, propylene glycol dimethyl ether and their polymeric forms such as triethylene glycol diethyl ether. Suitable ethanol solutions comprise any suitable ethanol- soluble inorganic or organic solute exemplified above as the solute as well as other polar solutes which are insoluble in water but soluble in ethanol such as 2-ethyl-1,3hexanediol, N,N-diethyltoluamide and 2-ethylhexyl-p-dimethylaminobenzoate. Emulsion compositions of this invention wherein the polar liquid comprises propylene glycol and glycerin and/or water are particularly useful.

PETROLATUM (b)

Petrolatum (b) suitable for use in the present invention comprises any grade of white or yellow petrolatum which is recognized as being safe for application to the human skin. The preferred type is white petrolatum. In general, any viscosity or consistency grade of petrolatum recognized in the art can be employed in the present invention.

CYCLIC POLYDIMETHYLSILOXANE FLUID (c)

Cyclic polydimethylsiloxane fluid (c) of the compositions of this invention have the formula $[(CH_3)_2SiO]_x$, wherein x denotes an integer of from 3 to 6. Such cyclic polydimethylsiloxanes typically have a boiling point of less than 250° C. and have a viscosity at 25° C. of less than 10 centipose. Cyclic polydimethylsiloxanes are well known, commercially available products. A highly preferred cyclic polydimethylsiloxane fluid is a mixture of said cyclic polydimethylsiloxanes wherein x is 4 or 5. Emulsion compositions of this invention may contain from 1 to 20 weight percent of cyclic polydimethylsiloxane fluid. Generally, it is preferred to employ from 10–15 weight percent of cyclic polydimethylsiloxane fluid in the emulsions of the present invention to provide the most improved aesthetics with minimum compatibility problems.

CROSSLINKED ORGANOPOLYSILOXANE-POLYOXYALKYLENE (d)

Component (d) is a crosslinked organopolysiloxane-polyoxyalkylene emulsifier having the formula:

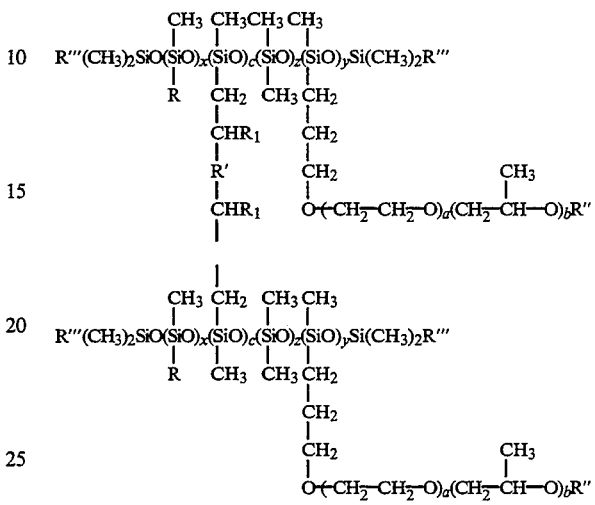

wherein

R is an aliphatic radical having 2 to 25 carbon atoms;

R' is an organic or organosiloxane group which does not contain hydrolyzable bonds;

R" is a terminal group;

R''' is independently an aliphatic radical having 1 to 25 carbon atoms;

$R_1$ is independently selected from the group consisting of hydrogen and an aliphatic radical containing 1–3 carbon atoms; x is an integer from 0 to 100;

c is an integer from 1 to 5;

z is an integer from 0 to 600;

y is an integer from 1 to 10;

$x+y+z \geq 40$;

a is an integer from 4 to 40;

b is an integer from 0 to 40; and $a/b \geq 1$.

The aliphatic radicals represented by R may include any of the $C_2$ to $C_{25}$ open-chain paraffin, olefin, and acetylenic hydrocarbons with parafinic hydrocarbons being preferred such as, for example, ethyl, propyl, hexyl, decyl, dodecyl and octadecyl.

The organic groups represented by R' may include for example $C_1$ to $C_{10}$ alkylene radicals such as methylene, dimethylene, trimethylene, pentamethylene and decamethylene; cycloalkylene radicals such as cyclohexylene; divalent aromatic radicals such as p-phenylene or o-phenylene; and oxygen containing radicals such as —COO $CH_2CH_2OOC$— and —$CH_2OCH_2$—.

The terminal group represented by R" may include acyl radicals of $C_1$ to $C_{20}$, for example, acetyl, propionyl, butyryl, isobutyryl, lauroyl, myristoyl, and stearoyl 3-carboxypentadecanoyl; alkyl radicals of $C_1$ to $C_{10}$ such as methyl, ethyl, propyl, butyl, and decyl; and the hydrogen atom. Other terminating groups possessing substantially the same properties as the above illustrative examples and which are prepared in a similar manner and which function in an equivalent manner may also be used.

The aliphatic radical represented by R''' may include any of the radicals illustrated above for R, but also include the methyl radical.

The unit of the crosslinking radical represented by $R_1$ may include hydrogen and monovalent $C_1$ to $C_3$ aliphatic radicals such as methyl, ethyl and propyl.

The preferred bridge bond of the crosslinked organopolysiloxane-polyoxyalkylene of the present invention is a saturated carbon-silicon bond which is not hydrolyzable and is highly stable. The organic or organo siloxane body R' of the crosslinking bridge is selected to be free of hydrolyzable bonds. It is also important that it be free of reactive sites which would react with ingredients incorporated into the emulsion to be emulsified. Further, R' should not interfere with the organopolysiloxane-polyoxyalkylene formation in any way.

A preferred crosslinking radical is a vinyl terminated organosiloxane. An organosiloxane bridge cooperates with the siloxane backbones which it bridges to create a siloxane network at the interface of water and oil in the emulsion. This network is thought to be important in effecting the stabilizing properties and characteristic of the present invention. The most preferred organo siloxane crosslinking material is tetramethyldivinyldisiloxane of the following formula:

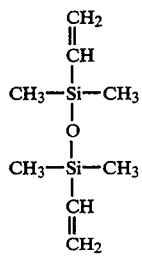

The organopolysiloxane-polyoxyalkylene molecules which are crosslinked must be soluble in the continuous or oil phase. If the organopolysiloxane-polyoxyalkylene is readily dispersible in the oil phase in a manner comparable to solubility, it is also considered "soluble". In order to effect such oil solubility, the characteristics of the siloxane backbone may be muted either by the presence of aliphatic radicals appended to the siloxane backbone, or by the presence of a significant number of dimethyl siloxane groups in the siloxane chain, or both. The appended polyoxyalkylene groups also enhance oil solubility, though a quantity of either the dimethyl siloxane groups, the aliphatic groups or both are required in excess of the number of polyoxyalkylene groups included in the molecule. Hence, the number of siloxane groups to which an aliphatic radical is appended is from 0 to 100. The number of dimethyl siloxane groups is from 0 to 600. The number of polyoxyalkylene appended siloxane groups is from 1 to 10. The combined total of those three different types of organo substituted siloxane groups is at least 40, thereby requiring at least Some dimethyl siloxane groups or aliphatic siloxane groups, or both in addition to the polyoxyalkylene siloxane groups.

The general formula of the preferred embodiment crosslinked organopolysiloxane-polyoxyalkylene illustrates two organopolysiloxane-polyoxyalkylene molecules bridged by a single linking radical. However, where C is greater than 1, there may be more than one crosslinking bridge between adjacent organopolysiloxane-polyoxyalkylene molecules, and/or there may be more than two organopolysiloxane-poly-oxyalkylene molecules linked together in the manner set forth below:

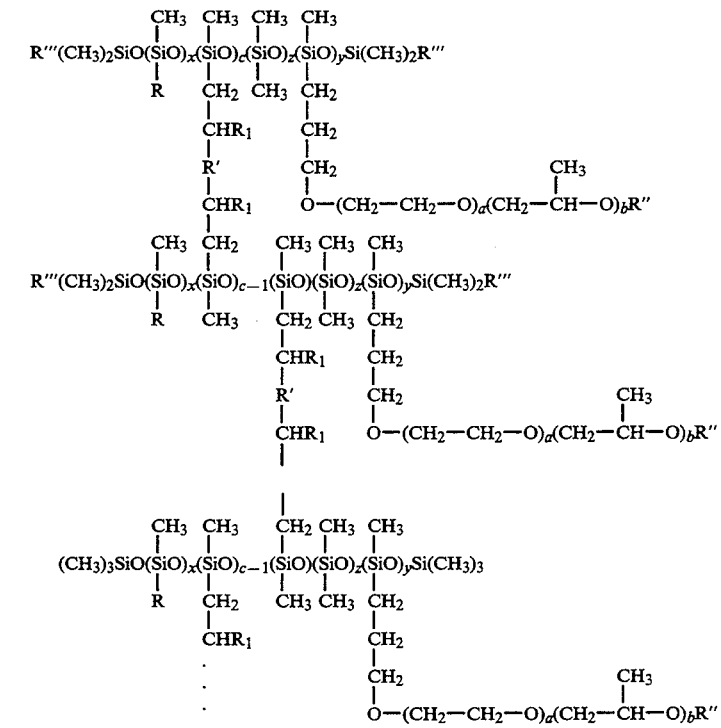

The exact number of organopolysiloxane-polyoxyalkylene polymer molecules which will be bridged together will be no more than 6. One limitation on such crosslinking is that the overall molecular weight must not become so great as to cause the material to gel. The extent of crosslinking must also be regulated relative to the molecular weight of each individual organopolysiloxane-polyoxyalkylene polymer molecule being crosslinked since the overall molecular weight must also be maintained sufficiently low to avoid gelling. A higher molecular weight in each individual polymer unit would require that there be less multiple crosslinking between units.

In the broadest aspects of the invention, it can be said that there are from 1 to 5 crosslinking bridges between 2 polymers, or where C is greater than 1, crosslinking bridges between 3 to 6 polymer units.

The preparation and further description for these crosslinked organopolysiloxane-polyoxyalkylene polymers is described in U.S. Pat. No. 4,853,474, which is incorporated herein by reference.

NON-CROSSLINKED POLYDIORGANOSILOXANE-POLYOXYALKYLENE (e)

In addition to the emulsifier of component (d), the present invention may contain additional emulsifiers. A preferred emulsifier to be used in conjunction with component (d) is a non-crosslinked polydiorganosiloxane-polyoxyalkylene copolymer (e) containing at least one polydiorganosiloxane segment and at least one polyoxyalkylene segment. The polyoxyalkylene segments may be bonded to the polydiorganosiloxane segments with silicon-oxygen-carbon bonds and/or with silicon-carbon bonds. A silicon-carbon bond is preferred.

The polydiorganosiloxane segments of the non-crosslinked polydiorganosiloxane-polyoxyalkylene copolymer (e) consist essentially of siloxane units which are interlinked by Si-O-Si linkages and which have the formula $R_b SiO_{(4-b/2)}$. The value of b may range from 0 to 3 for said siloxane units with the provision that there is an average of approximately 2, i.e. from 1.9 to 2.1 R radicals for every silicon in the copolymer. Suitable siloxane units thus include $R_3SiO_{\frac{1}{2}}$, $R_2SiO_{2/2}$, $RSiO_{3/2}$, and $SiO_{4/2}$ siloxane units taken in such molar amounts so that b has an average value of approximately 2 in the copolymer. The siloxane units may be arranged in linear, cyclic and/or branched fashion.

The R radicals in the non-crosslinked polydiorganosiloxane-polyoxyalkylene copolymer (e) may be any radical selected from the group consisting of methyl, ethyl, vinyl, phenyl, and a divalent radical bonding a polyoxyalkylene segment to the polydiorganosiloxane segment. At least 95 percent of all R radicals in the copolymer (e) are methyl radicals; preferably there is at least one methyl radical bonded to each silicon atom in (e). Divalent R radicals preferably contain no more than 6 carbon atoms. Examples of divalent R radicals include —O—, —$C_mH_{2m}O$—, —$C_mH_{2m}$— and —$C_mH_{2m}CO_2$— where m is an integer greater than zero.

Illustrative of the siloxane units that make up the polydiorganosiloxane segments of the non-crosslinked polydiorganosiloxane-polyoxyalkylene copolymer (e) are the following, where Me denotes methyl and Q denotes said divalent R radical and bonded polyoxyalkylene segment: $R_3SiO_{\frac{1}{2}}$ units such as $Me_3SiO_{\frac{1}{2}}$, $Me_2(CH_2=CH)SiO_{\frac{1}{2}}$, $Me_2(C_6H_5)SiO_{\frac{1}{2}}$, $Me(C_6H_5)(CH_2=CH)SiO_{\frac{1}{2}}$, $Me_2(CH_3CH_2)SiO_{\frac{1}{2}}$, $Me_2QSiO_{\frac{1}{2}}$, $MeQ_2SiO_{\frac{1}{2}}$, $Q_3SiO_{\frac{1}{2}}$, $Q_2(CH_3CH_2)SiO_{\frac{1}{2}}$, and $Me(C_6H_5)(Q)SiO_{\frac{1}{2}}$; $R_2SiO_{2/2}$ units such as $Me_2SiO_{2/2}$, $Me(C_6H_5)SiO_{2/2}$, $Me(CH_2=CH)SiO_{2/2}$, $(C_6H_5)_2SiO_{2/2}$, $MeQSiO_{2/2}$, and $Q(C_6H_5)SiO_{2/2}$; $RSiO_{3/2}$ units such as $MeSiO_{3/2}$, $C_6H_5SiO_{3/2}$, $CH_2=CHSiO_{3/2}$, $CH_3CH_2SiO_{3/2}$ and $QSiO_{3/2}$; and $SiO_{4/2}$ units.

It is to be understood that the non-crosslinked polydiorganosiloxane-polyoxyalkylene copolymer (e) may comprise one or more of said polydiorganosiloxane segments. The number and average molecular weight of the polydiorganosiloxane segments in the copolymer is related to the desired weight ratio, hereinafter described, of said segments in the copolymer. Preferably copolymer (e) comprises one polydiorganosiloxane segment having bonded thereto one or more polyoxyalkylene segments.

The polyoxyalkylene segments of the non-crosslinked polydiorganosiloxane-polyoxyalkylene copolymer (e) consist essentially of oxyethylene units of the formula —$CH_2CH_2O$—, alone, or in combination with oxypropylene units of the formula —$CH_2CH(CH_3)O$—, an average of at least half of the oxyalkylene units in the polyoxyalkylene segments being oxyethylene units. Thus the polyoxyalkylene segments correspond to the formula $\{-CH_2CH_2O-\}_p\{-CH_2CH(CH_3)O-\}_q$ wherein the oxyalkylene units may be arranged in any suitable fashion such as random, alternating and block. The average values of p and q are such that $p \geq q$ and the sum of p+q is sufficient to provide an average molecular weight of at least 1,000 for the polyoxyalkylene segments. Preferably the average molecular weight of the polyoxyalkylene segments has a value of from 1,500 to 5,000.

The polyoxyalkylene segments of the non-crosslinked polydiorganosiloxane-polyoxyalkylene copolymer (e) are bonded to the polydiorganosiloxane segments of said copolymer by at least one terminal portion of said polyoxyalkylene segment, said bonding being by way of a divalent R radical, hereinbefore described. The bonding may be by both terminal portions of said polyoxyalkylene segment in those copolymers comprising more than one polydiorganosiloxane segments. Any terminal portion of the polyoxyalkylene segment of the copolymer (e) that is not bonded to a polydiorganosiloxane is satisfied by a terminating radical. The type of said terminating radical is not critical and may be monovalent, thereby terminating one polyoxyalkylene segment, or polyvalent, thereby terminating more than one polyoxyalkylene segment. The terminating radicals are made up of atoms selected from the group consisting of carbon, hydrogen, nitrogen and oxygen. Illustrative of said terminating radical are hydrogen; hydroxyl; alkyl, such as methyl, ethyl, propyl, butyl; benzyl; aryl, such as phenyl; alkoxy, such as methoxy, ethoxy, propoxy, butoxy; benzyloxy; aryloxy, such as phenoxy; alkenyloxy, such as vinyloxy and allyloxy; acyloxy, such as acetoxy, acryloxy and propionoxy and amino, such as dimethylamino.

The number and average molecular weights of the segments in the non-crosslinked polydiorganosiloxane-polyoxyalkylene copolymer (e) are such that the weight ratio of polydiorganosiloxane segments to polyoxyalkylene segments in copolymer (e) has a value of from 2 to 8, and preferably from 2.5 to 4.0. The weight ratio of polydiorganosiloxane segments to polyoxyalkylene segments is calculated on the basis of the total weight of polydiorganosiloxane and the total weight of polyoxyalkylene that is joined in the copolymerization process. For example, if 100 parts by weight of polydiorganosiloxane is joined completely by an addition process, which utilizes silicon-bonded hydrogen radicals, with 20 parts by weight of polyoxyalkylene, said weight ratio of the resulting copolymer has a value of 5. If said complete joining is accomplished by a displacement reaction, involving a silicon-bonded hydrolyzable radical and resulting in the formation of a by-product, the weight ratio of polydiorganosiloxane to polyoxyalkylene in the resulting copolymer may not be identical with the weight ratio of the corresponding reactants, due to the loss of the weight of the displaced groups. The error introduced into the calculation of said weight ratio by ignoring the loss of said displaced groups is usually insignificant. That is to say, the weight ratio of polydiorganosiloxane to polyoxyalkylene in copolymer (e) may be calculated from the weight of reactants that react to form the copolymer or said weight ratio may be determined by suitable analysis of the resulting copolymer itself.

Herein, copolymer means either a block arrangement of segments such as denoted by the formula $(AB)_c$, $A(BA)_c$ and $B(AB)_c$ or a pendant arrangement of segments such as $(AB_d)_c$ or combinations thereof wherein A denotes a polyoxyalkylene segment and c and d denote integers greater than zero and greater than one, respectively.

The non-crosslinked polydiorganosiloxane-polyoxyalkylene copolymers (e) may be prepared by modifications of the well-known methods described in the polydiorganosiloxane-polyoxyalkylene copolymer art. The following patents are hereby incorporated by reference to show the preparation of polydiorganosiloxane-polyoxyalkylene copolymers: Haluska, U.S. Pat. No. 2,868,824 and Gee et al., U.S. Pat. No. 4,122,029.

A non-essential component which may be incorporated into the compositions of this invention is a silicone gum. Silicone gums are defined in U.S. Pat. No. 4,152,416, which is hereby incorporated by reference. Briefly, this patent discloses silicone gums having a viscosity within the range from 500,000 to 100 million centistokes at 25° C. Such silicone gums, for example, polydimethylsiloxane polymers, as disclosed in U.S. Pat. No. 4,152,416 are also applicable in the present invention. A preferred silicone gum is Dow Corning Q2-1401 fluid, containing 86–88 percent by weight of a cyclic dimethyl polysiloxane, also referred to as cyclomethicone, and 12–14% by weight of dimethyl silicone terminated with hydroxyl groups, also referred to as dimethiconol.

Other non-essential components which are common to personal-care compositions of the art, such as fragrances, perfumes, humectants, preservatives and colorants may be incorporated into the compositions of this invention provided they do not destabilize the emulsion so as to cause a breaking or an inverting of the emulsion.

The emulsion compositions of this invention can comprise from about 1 to about 75, preferably from about 50 to about 75 percent by weight of the discontinuous phase, from about 5 to about 50, preferably from about 20 to about 40 percent by weight of the continuous phase, and from about 0.2 to about 9, preferably from about 1 to 3 percent by weight of a crosslinked organopolysiloxane-polyoxyalkylene emulsifier in accordance with the present invention.

The emulsions of the present invention are prepared by preparing, separately, the indicated continuous phase and the indicated discontinuous phase and then slowly adding the discontinuous phase to the agitated continuous phase, followed by continued agitation of the resulting mixture until it becomes homogeneous. Agitation is accomplished by a propeller mixer or a homogenizer. Other methods of emulsion preparation which provide stable water-in-oil emulsions are suitable, but care must be taken to prevent inversion of the emulsion to an oil-in-water emulsion during its preparation.

In order that those skilled in the art may better understand how to practice the present invention, the following examples are given by way of illustration and not by way of limitation. All parts and percentages in the examples are on a weight basis.

Preparation of the crosslinked organopolysiloxane-polyoxyalkylene emulsifier (d)

The crosslinked organopolysiloxane-polyoxyalkylene, component (d), used in the following examples, and designated as "Emulsifier I" in Table I, was prepared based on the following formulation:

| | |
|---|---|
| 15.7% | $ME_3SiO(MEHSiO)_{41(30-60)}SiME_3$ |
| 36.2% | 1st dodecene addition |
| 15.0% | 2nd dodecene addition |
| 9.0% | Isostearyl alcohol |
| 23.6% | $CH_2{=}CHCH_2(OCH_2CH_2)_{19}(OCH_2\overset{\underset{\displaystyle CH_3}{\mid}}{C}H)_{19}{-}OH$ (preneutralized pH 7–8) |
| 0.5% | $CH_2{=}CH\underset{\underset{\displaystyle CH_3}{\mid}}{\overset{\overset{\displaystyle CH_3}{\mid}}{Si}}{-}O{-}\underset{\underset{\displaystyle CH_3}{\mid}}{\overset{\overset{\displaystyle CH_3}{\mid}}{Si}}CH{=}CH_2$ |
| 14 ppm | Pt. (chloroplatinic acid (2% $H_2PtCl_6$ $6H_2O$)/IPA) hydrosilation catalyst |

As will be appreciated by those skilled in the art, the siloxane backbone material actually includes a mixture in which the methyl siloxane hydride units may comprise anywhere from approximately 30 to approximately 60 units on a given siloxane molecule. However, the mean was approximately 41 as indicated.

The dodecene was at 91% olefinic activity. The indicated percentages are by weight. The indicated pH of the vinyl polyoxyalkylene glycol was determined based on a 15% by weight solution thereof in water.

All of the siloxane backbone material and 10% of the first dodecene addition was loaded into the reactor with agitation and the pressure was reduced by about 25 millimeters of mercury for one minute, after which the vessel was backfilled with nitrogen. With a nitrogen sweep, the mixture was heated to 85° C. and 25 percent of the catalyst solution and the remainder of the first dodecene addition were added over a period of two to three hours holding the temperature at 105° to 115° C. After all of the first dodecene addition was completed, the vessel was held at 110° C. for 15 minutes.

The temperature was then dropped to 80° C. and all of the divinyltetramethylsiloxane crosslinking agent was added along with an additional 25 percent of the catalyst solution. The vessel reaction temperature was returned to 110° C. and held there for 15 minutes.

At this point, the isostearyl alcohol was added along with the vinyl polyoxyalkylene. The vessel was again degassed and backfilled as in the first step described above. Another 30 percent of the catalyst solution was added and the temperature increased to 110° C. and held there for 30 minutes. The material was clear.

The remainder of the catalyst was then added to the vessel and it was heated to 120° C. and held there for 30 minutes. The second dodecene addition was then made and the vessel was held at 120° C. for an additional hour. Thereafter, the composition was cooled and removed from the reaction vessel.

The resulting emulsifier had the following general formula:

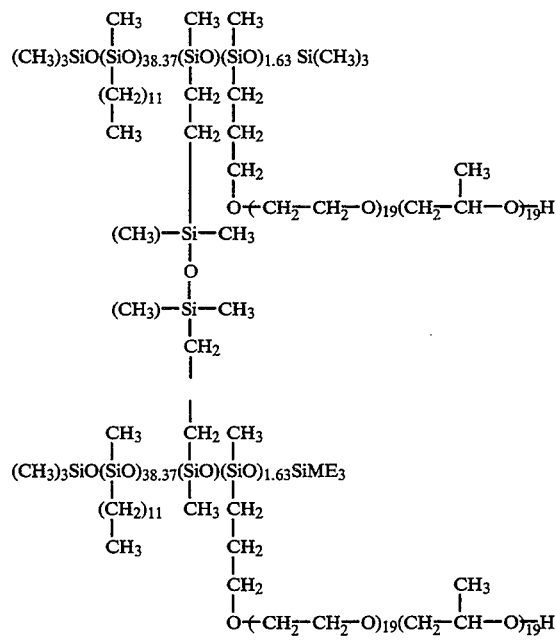

Thus, the emulsifier of this example included no dimethyl siloxane groups, but an average of 38.37 aliphatic added siloxane groups. The numerical values indicated were calculated based on starting ingredients. The divinyl disiloxane was added at only about 0.5 percent by weight, creating one cross link per polymer.

Preparation of the non-crosslinked polydiorganosiloxane-polyoxyalkylene copolymer (e)

The non-cross linked polydiorganosiloxane-polyoxyalkylene copolymer (e) that was used in the following examples, and designated as "Emulsifier II" in Table I, was prepared from a trimethylsiloxane-endblocked polydimethylsiloxane having a molecular weight of approximately 30,000 and an average of approximately 4 of its dimethylsiloxane units replaced with methylhydrogensiloxane units, and a random equimolar polyglycol copolymer of ethylene oxide and propylene oxide having an average molecular weight of approximately 2550 and having allyloxy endgroups on one end and acetoxy endgroups on the other end. Two hundred twenty grams of the siloxane, 80.76 grams of the polyglycol and 75.19 grams of isopropanol were mixed and heated to reflux under dry nitrogen in a flask and the resulting solution was catalyzed with 0.15 ml. of a 1 molar solution of $H_2PtCl_6$ in isopropanol. The reaction mixture was heated at reflux for one hour and then devolatilized at 110° C. and 1.33 kilopascals pressure. The non-crosslinked polydimethylsiloxane-polyoxyalkylene copolymer product had a siloxane/oxyalkylene weight ratio of approximately 2.7 and $-CH_2CH_2CH_2O-$ divalent radicals bonding the polyoxyalkylene portion to the polydimethylsiloxane portion by way of a silicon-carbon bond.

EXAMPLES 1–35

The emulsion compositions that are described in the following examples were prepared by combining white petrolatum, a cyclic polydimethylsiloxane fluid having the average formula $[(CH_3)_2SiO]_{14}$, a crosslinked organopolysiloxane-polyoxyalkylene emulsifier, as described above, and/or a non-crosslinked polydiorganosiloxane- polyoxyalkylene copolymer, as described above, and/or Dow Corning Q2-1401 fluid containing 87% by weight cyclomethicone and 13% by weight dimethiconol, to form a Mixture (I). The refractive index of Mixture (I) was determined by using a refractometer and is listed in Table I. Separately, propylene glycol and in some examples glycerin and/or water with 1% sodium chloride dissolved therein, were combined to form a Mixture (II). The refractive index of Mixture (II) was determined by using a refractometer and is listed in Table I. Mixture (II) was slowly added to Mixture (I) while agitation was applied to Mixture (I) by means of a propeller mixer. Agitation was continued after addition of Mixture (II) until homogeneity was attained. The indicated amounts of each component for each example are listed in Table I.

TABLE I

| | CONTINUOUS PHASE | | | | | DISCONTINUOUS PHASE | | | |
|---|---|---|---|---|---|---|---|---|---|
| Petro-latum | Cyclic Polydimethyl Siloxane | Dow Corning Q2-1401 | Emulsifier II | Emulsifier I | Refractive Index | H2O (with 1% NaCl) | Gly-cerine | Propylene Glycol | Refractive Index |
| 1  | 15 | 0  | 0 | 15 | 0 | 1.434 | 0  | 0  | 70 | 1.433 |
| 2  | 15 | 0  | 0 | 15 | 0 | 1.434 | 20 | 50 | 0  | 1.434 |
| 3  | 10 | 0  | 0 | 20 | 0 | 1.422 | 8  | 0  | 62 | 1.422 |
| 4  | 10 | 0  | 0 | 20 | 0 | 1.422 | 26 | 44 | 0  | 1.422 |
| 5  | 15 | 8  | 0 | 5  | 2 | 1.437 | 15 | 43 | 12 | 1.437 |
| 6  | 15 | 10 | 0 | 3  | 2 | 1.436 | 15 | 41 | 14 | 1.436 |
| 7  | 15 | 10 | 0 | 3  | 2 | 1.436 | 10 | 29 | 31 | 1.436 |
| 8  | 15 | 13 | 0 | 0  | 2 | 1.436 | 10 | 29 | 31 | 1.436 |
| 9  | 20 | 13 | 0 | 0  | 2 | 1.441 | 8  | 32 | 25 | 1.441 |
| 10 | 20 | 13 | 0 | 0  | 2 | 1.441 | 5  | 25 | 35 | 1.441 |
| 11 | 12 | 8  | 0 | 10 | 0 | 1.426 | 15 | 24 | 31 | 1.426 |
| 12 | 12 | 11 | 0 | 5  | 2 | 1.429 | 13 | 25 | 32 | 1.429 |
| 13 | 12 | 13 | 0 | 3  | 2 | 1.429 | 13 | 25 | 32 | 1.429 |
| 14 | 12 | 16 | 0 | 0  | 2 | 1.428 | 13 | 23 | 34 | 1.428 |
| 15 | 15 | 3  | 0 | 8  | 1 | 1.440 | 10 | 36 | 27 | 1.440 |
| 16 | 15 | 3  | 0 | 8  | 1 | 1.440 | 0  | 12 | 61 | 1.440 |
| 17 | 15 | 3  | 0 | 8  | 1 | 1.440 | 0  | 0  | 73 | 1.433 |
| 18 | 15 | 13 | 0 | 0  | 2 | 1.436 | 10 | 29 | 31 | 1.436 |

TABLE I-continued

| | | CONTINUOUS PHASE | | | | | DISCONTINUOUS PHASE | | | |
|---|---|---|---|---|---|---|---|---|---|---|
| | Petrolatum | Cyclic Polydimethyl Siloxane | Dow Corning Q2-1401 | Emulsifier II | Emulsifier I | Refractive Index | H2O (with 1% NaCl) | Glycerine | Propylene Glycol | Refractive Index |
| 19 | 15 | 13 | 2 | 0 | 2 | 1.433 | 10 | 24 | 34 | 1.433 |
| 20 | 15 | 10 | 2 | 0 | 2 | 1.438 | 10 | 31 | 30 | 1.437 |
| 21 | 15 | 9 | 2 | 0 | 2 | 1.439 | 10 | 34 | 28 | 1.439 |
| 22 | 15 | 11 | 2 | 0 | 2 | 1.436 | 0 | 5 | 65 | 1.436 |
| 23 | 15 | 1 | 2 | 12 | 0 | 1.434 | 0 | 2 | 68 | 1.434 |
| 24 | 18 | 8 | 0 | 0 | 2 | 1.447 | 10 | 49 | 13 | 1.447 |
| 25 | 20 | 6 | 0 | 0 | 2 | 1.452 | 10 | 57 | 5 | 1.452 |
| 26 | 13 | 11 | 2 | 0 | 2 | 1.434 | 10 | 26 | 36 | 1.434 |
| 27 | 15 | 10.25 | 2 | 0 | 0.75 | 1.436 | 10 | 30 | 32 | 1.436 |
| 28 | 15 | 10 | 2 | 0 | 1 | 1.437 | 10 | 31 | 31 | 1.437 |
| 29 | 15 | 9.5 | 2 | 0 | 1.5 | 1.438 | 10 | 33 | 29 | 1.438 |
| 30 | 15 | 10 | 2 | 0 | 1 | 1.437 | 7 | 24 | 41 | 1.437 |
| 31 | 15 | 10 | 2 | 0 | 1 | 1.437 | 5 | 18 | 49 | 1.436 |
| 32 | 15 | 10 | 2 | 0 | 2 | 1.438 | 5 | 20 | 47 | 1.438 |
| 33 | 15 | 12 | 0 | 0 | 2 | 1.437 | 5 | 19 | 48 | 1.437 |
| 34 | 15 | 12 | 0 | 0 | 2 | 1.437 | 0 | 7 | 64 | 1.437 |
| 35 | 15 | 12.5 | 0 | 0 | 1.5 | 1.436 | 0 | 6 | 65 | 1.436 |

Other embodiments of the invention will be apparent to the skilled in the art from a consideration of this specification or practice of the invention disclosed herein. It is intended that the specification and examples be considered as exemplary only, with the true scope and spirit of the invention being indicated by the following claims.

What is claimed is:

1. An emulsion comprising 1-75 percent by weight of a discontinuous phase comprising a polar liquid; and 5-50 percent by weight of a continuous phase comprising petrolatum, 1-20 percent by weight of a cyclic polydimethylsiloxane fluid, and 0.2-9 percent by weight of a crosslinked emulsifier in which at least two organopolysiloxane-polyoxyalkylene molecules are crosslinked by a crosslinking radical; the discontinuous phase and the continuous phase having refractive index measurements which are matched within 0.01 to provide translucency, the crosslinked organopolysiloxane-polyoxyalkylene emulsifier having the formula:

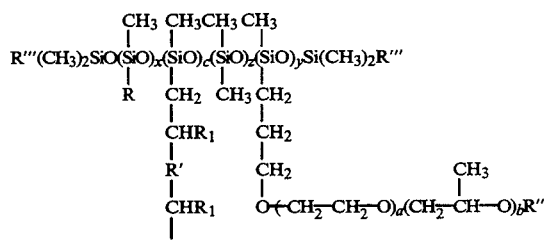

-continued

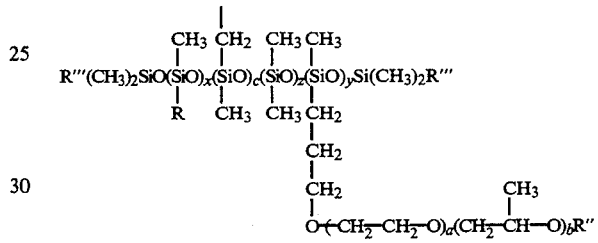

wherein

R is an aliphatic radical having 2 to 25 carbon atoms;

R' is an organic or organosiloxane group which does not contain bydrolyzabe bonds;

R" is a terminal group;

R''' is independently an aliphatic radical having 1 to 25 carbon atoms;

R1 is independently selected from the group consisting of hydrogen and an aliphatic radical containing 1-3 carbon atoms; x is an integer from 0 to 100; c is an integer from 1 to 5;

z is an integer from 0 to 600;

y is an integer from 1 to 10;

x+y+z>40;

a is an integer from 4 to 40;

b is an integer from 0 to 40;

a/b>1, and in which the cyclic polydimethylsiloxane fluid has the formula [(CH3)2SiO]x wherein x is an integer having a value of 3-6.

2. An emulsion according to claim 1 in which the continuous phase includes a non-crosslinked emulsifier which is a polydiorganosiloxane-polyoxyalkylene copolymer containing at least one polydiorganosiloxane segment and at least one polyoxyalkylene segment.

3. An emulsion according to claim 1 in which the continuous phase includes a silicone gum having a viscosity of 500,000-100,000,000 centistokes measured at twenty-five degrees Centigrade.

4. An emulsion according to claim 2 in which the continuous phase includes a silicone gum having a viscosity of 500,000-100,000,000 centistokes measured at twenty-five degrees Centigrade.

* * * * *